United States Patent [19]
Watt et al.

[11] Patent Number: 5,123,427
[45] Date of Patent: Jun. 23, 1992

[54] PERSON SUPPORT

[76] Inventors: Jerry L. Watt, R.R. #2, Wapakoneta, Ohio 45895; Dennis J. Watt, Box 7172, Lafayette, Ohio 45854

[21] Appl. No.: 701,063
[22] Filed: May 16, 1991
[51] Int. Cl.$^5$ .............................................. A61F 5/37
[52] U.S. Cl. .......................... 128/876; 128/DIG. 25
[58] Field of Search .......................... 128/874–876, 128/78, 99.1, DIG. 15; 2/49 R, DIG. 6; 297/465

[56] References Cited

U.S. PATENT DOCUMENTS

| | | | |
|---|---|---|---|
| 3,136,311 | 6/1964 | Lewis | 128/874 |
| 3,265,065 | 8/1966 | Jillson | 128/874 |
| 4,117,840 | 10/1978 | Rasure | 128/874 |
| 4,170,991 | 10/1979 | Kella | 128/876 |
| 4,487,201 | 12/1984 | Ciambarella | 128/876 |
| 4,639,946 | 2/1987 | Koenig | 2/49 R |
| 4,898,185 | 2/1990 | Fuller | 128/876 |
| 4,981,148 | 1/1991 | Fuller | 128/876 |
| 5,031,639 | 7/1991 | Wolfer | 128/874 |

Primary Examiner—Robert A. Hafer
Assistant Examiner—Michael Brown
Attorney, Agent, or Firm—Allen D. Gutchess, Jr.

[57] ABSTRACT

A positioner releasably positions a portion of a person's body relative to a supporting surface. The positioner includes a wide flexible band of sufficient length to encircle a portion of the person's body. The flexible band has accessible ends which have adjustable connections for connecting end portions of the band together around the body portion. An intermediate portion of the flexible band has a first velcro patch of predetermined size and shape facing away from the person's body. The positioner further includes a second velcro patch which is attached in a predetermined position on the supporting surface. When the patches are engaged, the positioner thus releasably supports the portion of the body relative to the supporting surface to aid in holding the body portion in position until the flexible band is released or until the two velcro patches are separated.

14 Claims, 2 Drawing Sheets

PERSON SUPPORT

This invention relates to a positioner for releasably positioning a portion of a person's body relative to a supporting surface.

The invention is particularly applicable to positioning a part of a patient's torso relative to a supporting back of a chair. A wide, flexible band is placed around the patient's torso, usually in the chest area, and the band has accessible ends with adjustable connecting means to enable the band to snugly encircle the patient's torso. An intermediate portion of the band has a first velcro patch of predetermined size and shape at the patient's back and facing away from the patient. A second velcro patch is attached to the back of the chair and facing away from the chair back in a position to engage the first velcro patch when the patient is sitting in a generally upright position in the chair. The second velcro patch has flexible straps or the like which extend around the chair back and are fastened together to hold the second velcro patch in the predetermined position. Preferably the first velcro patch contains loops and the second velcro patch contains hooks which are cooperable to releasably affix the patches together.

With this arrangement, the positioner in accordance with the invention aids in supporting the patient in the chair by providing support around the torso. However, the patient is not physically restrained so that he can separate himself from the chair or someone else can quickly do so at any desired time. The positioner is particularly advantageous when an emergency arises so that the patient can be quickly separated from the chair without the need to undo any buckles, straps, or the like.

The positioner in accordance with the invention can also be employed around a portion of a person's body to place the body portion temporarily in a predetermined position relative to a supporting surface. In such an instance, the one velcro patch has a band for encircling a portion of the person's body and a second velcro patch is attached in a predetermined position on a supporting surface. The two patches are then engaged with one another to position the person's body portion in a particular position.

It is, therefore, a principal object of the invention to provide a positioner for aiding in positioning a portion of a person's body in a predetermined position relative to a supporting surface.

Another object of the invention is to provide a patient positioner for aiding in releasably supporting a patient in a generally upright position in a chair or the like.

Many other objects and advantages of the invention will be apparent from the following detailed description of preferred embodiments thereof, reference being made to the accompanying drawings, in which.

Figure 1:
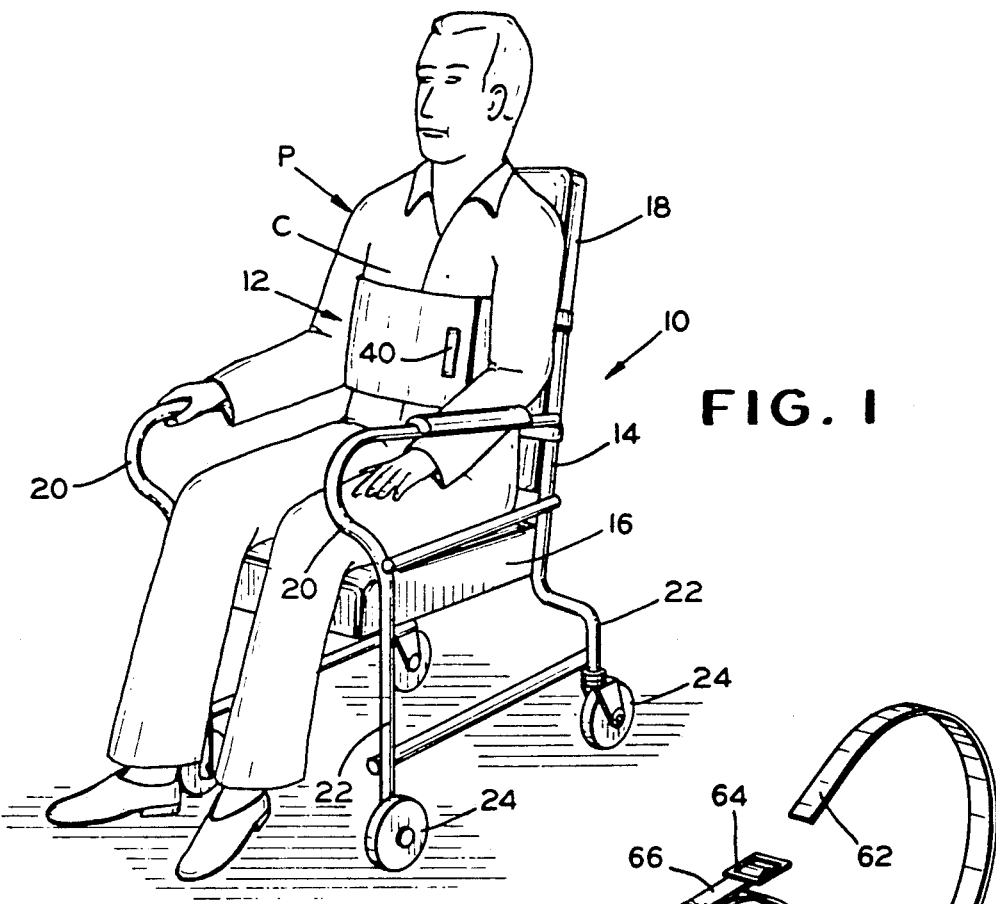
FIG. 1 is a somewhat schematic view in perspective of a patient in a chair being partially supported by a patient positioner in accordance with the invention.

Referring to the drawings, and more particularly to FIG. 1, an invalid chair 10 is shown with a patient or person P seated therein with a patient or person positioner 12 shown in operational condition. The chair 10 is of a type commonly found in nursing homes, with an elderly person or invalid often sitting or languishing in the chair for extended periods of time. The chair basically includes a framework 14, a seat 16, a back 18, arms 20, legs 22, and wheels 24. A retractable foot rest (not shown) is also usually employed. With this type of chair, the person can be transported from a bedroom to an eating area or lounge, for example, without the necessity of being transferred to a wheelchair and back again.

The person positioner 12 aids in supporting a portion of the patient P, and specifically an upper portion or chest C of his torso, in a predetermined position relative to a supporting surface, and specifically the back 18 of the chair 10. The positioner 12 basically includes two separate and separable components, namely a person component 26 and a support component 28. The component 26 includes a flexible, wide band 30 having free ends 32 and 34 which are accessible in front of the portion of the person around which the band 30 extends, encircling that portion. The free ends 32 and 34 have adjustable connections 36 and 38 for connecting the free ends of the band 30 together to adjust the length of the band and enabling it to snugly fit around the person's portion, and specifically the chest C of the patient P in this instance. As shown, the adjustable connections include cooperating commercially-available velcro patches, with the connection 36 being the hook portion of the fastener and the connection 38 being the loop portion, in this instance. Other patches similar to velcro may be used or various adjustable buckles can be employed. The front surface of the flexible band 30 opposite the fastener 36 has a loop or strap 40 (FIG. 1) to facilitate the addition of a separate strap around the patient and the chair if the patient needs to be physically restrained.

The flexible band 30, in this instance, has a wider intermediate part 42 on the back of which is affixed a large patch of velcro, preferably the loop part thereof, indicated at 44. In this instance, the patch 44 is affixed to the wide part 42 by peripheral stitches and horizontal stitches extending across a central portion of the patch.

Figure 2:
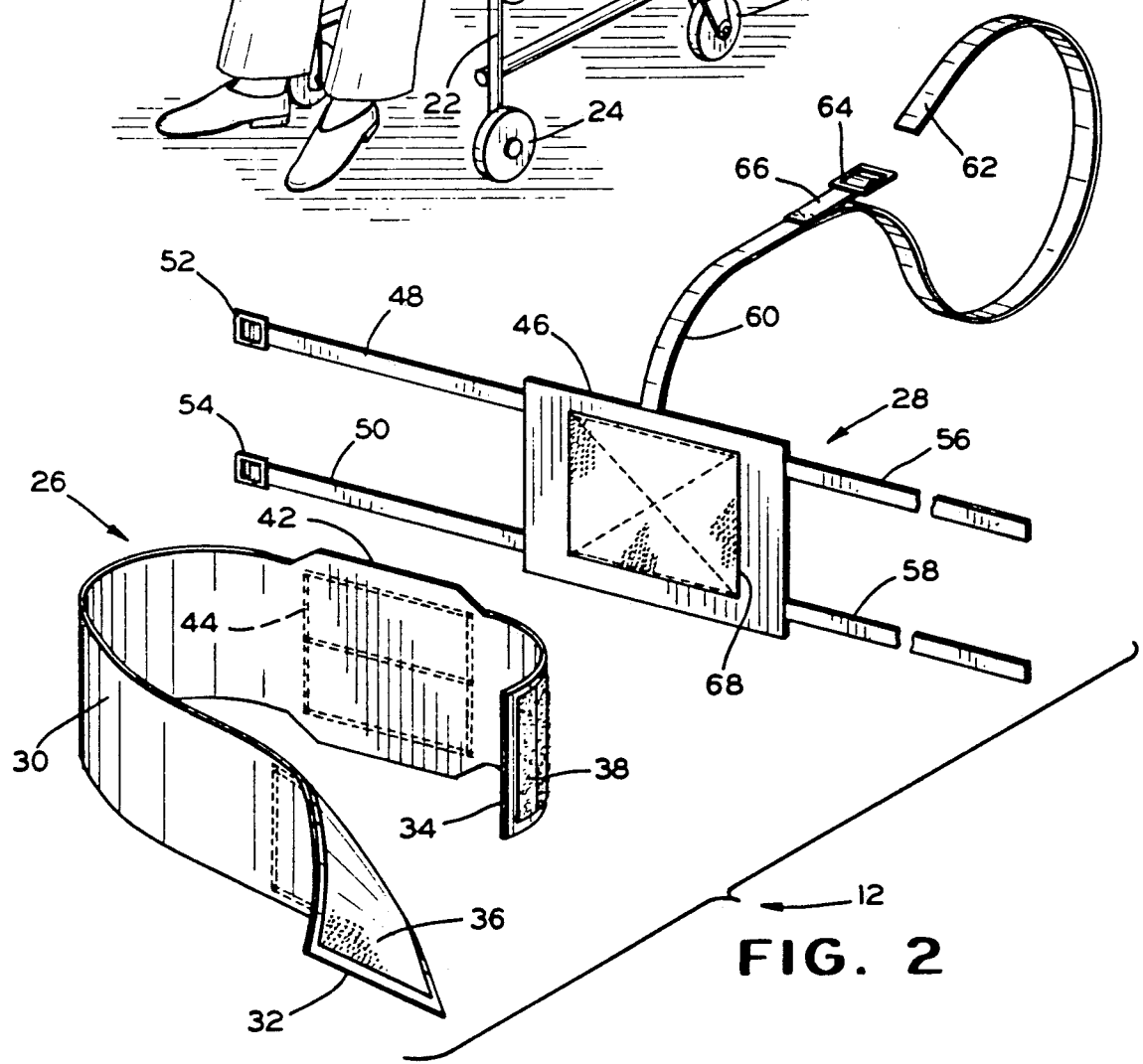
FIG. 2 is an exploded view in perspective of the patient positioner shown in FIG. 1.
Figure 3:
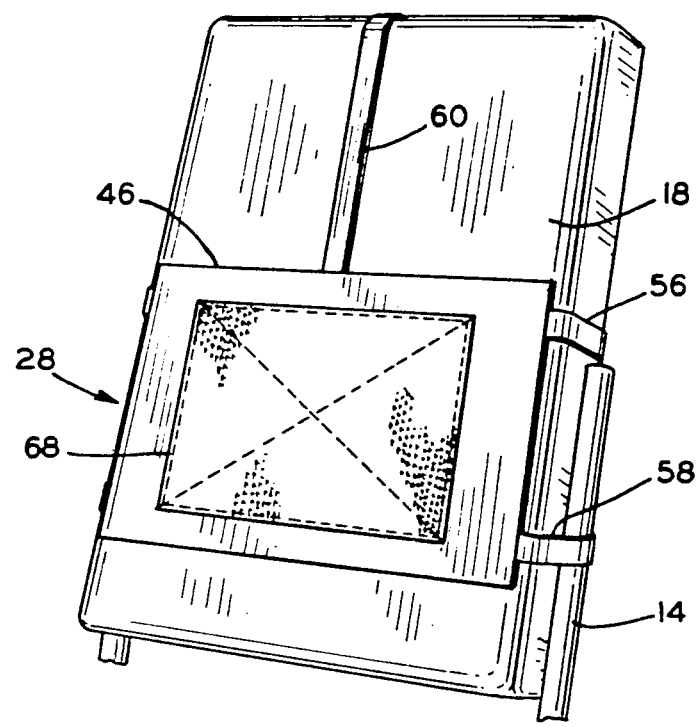
FIG. 3 is a view in perspective of a portion of the patient positioner attached to the back of a chair.
Figure 4:
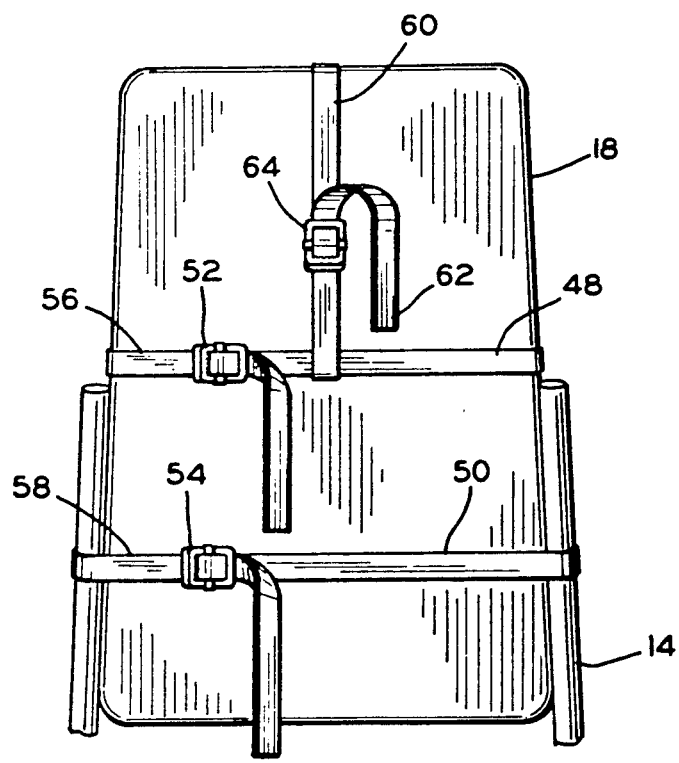
FIG. 4 is a rear view in elevation of a portion of the positioner and the chair back shown in FIG. 3.

Referring now to the component 28, it includes a fabric mounting base or means 46 (FIGS. 2 and 3) which extends across a substantial portion of the chair back 18. The base 46 has upper and lower straps 48 and 50 suitably affixed at an edge, as by stitching, and terminating in commercially-available adjustable fasteners or buckles 52 and 54. Additional upper and lower straps 56 and 58 are suitably affixed, as by stitching, to the other edge of the base 46 and extend in the opposite direction. The upper straps 48 and 56 and the lower straps 50 and 58 are then connected together by the buckles 52 and 54 and tightened to snugly affix the mounting base 46 on the chair back 18. However, before these are fully tightened, a vertical strap 60, which is suitably affixed, as by stitching, to an upper edge of the mounting base 46 is extended over the back of the chair. The strap 60 has a free end 62 which is extended around the upper strap 48 and adjustably connected to a commercially-available, adjustable fastener or buckle 64 which is mounted at an end of a short strap 66. The strap is affixed, in turn, to an intermediate portion of the strap 60, as by stitching. The mounting base 46 can be raised or lowered relative to the chair back 18 by manipulation of the strap end 62 and the buckle 64, before the upper straps 48, 56 and the lower straps 50, 58 are fully tightened.

A patch 68 of velcro, preferably the hook part thereof, is centrally affixed to the mounting base 46, as by peripheral and cross-stitching. The cooperating patches 44 and 68 preferably are of approximately the same size and shape and are positioned so that they are in substantially superimposed relationship when a patient, with the component 26 attached around the chest C of the torso, is seated on the chair and his back is moved toward the chair back 18 to place the patches 44 and 68 in cooperating, attaching relationship.

The connected patches provide resistance to being separated so that the positioner 12 maintains the chest portion of the patient in an upright position and substantially reduces slouching and slumping, which will often otherwise occur, particularly when an elderly patient is in the chair 10 for an extended period of time. It also substantially prevents the patient from falling out of the chair, as may occur if the patient is asleep or is being transported. At the same time, the patient P can separate himself from the chair 10, either with or without aid. Further, in an emergency, the patient can be quickly separated from the chair without the need for undoing straps and buckles or other fasteners.

The size and shape of the patches 44 and 68 will, of course, vary according to the particular application. If smaller bands corresponding to the bands 30 are employed around a patient's shoulders, for example, then two of the patches 68 can be located at upper edge portions of the chair to aid in better retaining the shoulders of the patient against the chair back.

Various modifications of the above-described embodiments of the invention will be apparent to those skilled in the art, and it is to be understood that such modifications can be made without departing from the scope of the invention, if they are within the spirit and the tenor of the accompanying claims.

We claim:

1. A patient support for aiding in supporting a patient in a general upright position in a chair having a seat and a back, said support comprising a flexible band of sufficient length to encircle a portion of the patient's body and having ends accessible generally in front of the patient's body, with the ends having adjustable connecting means for connecting end portions of the band together, an intermediate portion of said band to be positioned behind the patient's body having a first patch of predetermined size and shape and facing away from the patient, a second patch of predetermined size and shape substantially equal to the size and shape of said first patch, and means for attaching said second patch to the back of the chair, facing away from the chair back, and positioned to engage said first patch when the patient is sitting in a generally upright position in the chair, said attaching means including a mounting base of a size to extend across a substantial portion of the seat back, first upper and first lower straps affixed to one edge of said mounting base, with said straps terminating in adjustable fasteners, second upper and second lower straps affixed to another edge of said mounting base, said upper straps being connectable and said lower straps being connectable behind the chair back to snugly affix said mounting base to said chair back, a vertical strap affixed to an upper edge of said mounting base, said vertical strap having a free end which is extendable around said upper straps and having an adjustable fastener, said mounting base being raised or lowered by manipulation of the free end of the vertical strap relative to said upper straps before the upper and lower straps are fully tightened, and means affixing said second patch to a central portion of said mounting base.

2. A patient support according to claim 1 wherein one of said patches contains hooks and the other of said patches contains loops cooperable with said hooks to releasably affix said patches together.

3. A patient support according to claim 1 wherein said last-named means affixing said second patch to said mounting base comprises stitching.

4. A patient support according to claim 3 wherein said stitching comprises peripheral stitching and cross stitching.

5. A patient support according to claim 1 wherein said adjustable connecting means for said flexible band comprises a patch containing hooks connected to one end portion of said flexible band and a patch containing loops connected to another end portion of said flexible band.

6. A patient support according to claim 1 wherein said adjustable fasteners for said first upper and lower straps comprise buckles.

7. A patient support according to claim 1 wherein said first patch is affixed to the intermediate portion of said band by stitching.

8. A patient support according to claim 7 wherein said stitching includes peripheral stitching and additional stitching extending across a central portion of said first patch.

9. A patient support for aiding in supporting a patient in a general upright position in a chair having a seat and a back, said support comprising a flexible band of sufficient length to encircle a portion of the patient's body and having ends accessible generally in front of the patient's body, with the ends having adjustable connecting means for connecting end portions of the band together, an intermediate portion of said band to be positioned behind the patient's body having a first patch of predetermined size and shape and facing away from the patient, a second patch of predetermined size and shape similar to the size and shape of said first patch, and means for attaching said second patch to the back of the chair, facing away from the chair back, and positioned to engage said first patch when the patient is sitting in a generally upright position in the chair, said attaching means including a mounting base of a size to extend across a substantial portion of the seat back, said second patch extending over most of said mounting base, first upper and first lower straps affixed to one edge of said mounting base, with said straps terminating in adjustable fasteners, second upper and second lower straps affixed to another edge of said mounting base, said upper straps being connectable and said lower straps being connectable to snugly affix said mounting base to said chair back, a vertical strap affixed to an upper edge of said mounting base, said vertical strap extending over an upper edge of the chair back and having a free end which is extendable around said upper straps and having an adjustable fastener, said mounting base being raised and lowered by manipulation of the free end of the vertical strap relative to said upper straps before the upper and lower straps are fully tightened, and means for affixing said second patch to a central portion of said mounting base.

10. A patient support according to claim 9 wherein one of said patches contains hooks and the other of said patches contains loops cooperable with said hooks to releasably affix said patches together.

11. A patient support according to claim 9 wherein said last-named means affixing said second patch to said mounting base comprises stitching.

12. A patient support for aiding in supporting a patient in a general upright position in a chair having a seat and a back, said support comprising a flexible band of sufficient length to encircle a portion of the patient's body and having ends accessible generally in front of the patient's body, with the ends having adjustable means for connecting end portions of the band together, an intermediate portion of said band to be positioned behind the patient's body having a first patch of predetermined size and shape and facing away from the patient, a second patch of predetermined size and shape substantially equal to the size and shape of said first patch, and means for attaching said second patch to the back of the chair, facing away from the chair back, and positioned to engage said first patch when the patient is sitting in a generally upright position in the chair, said attaching means including a mounting base of a size to extend across a substantial portion of the seat back, first horizontal straps affixed to one edge of said mounting base, with said straps terminating in adjustable fasteners, second horizontal straps affixed to another edge of said mounting base, said horizontal straps being connectable behind the chair back to snugly affix said mounting base to said chair back, a vertical strap affixed to an upper edge of said mounting base, said vertical strap extending over an upper edge of the chair back and having a free end which is extendable around some of said horizontal straps and having an adjustable fastener, said mounting base being raised or lowered by manipulation of the free end of the vertical strap relative to said horizontal straps, and means for affixing said second patch to a central portion of said mounting base.

13. A patient support according to claim 12 wherein one of said patches contains hooks and the other of said patches contains loops cooperable with said hooks to releasably affix said patches together.

14. A patient support according to claim 12 wherein said last-named means affixing said second patch to said mounting base comprises stitching.

* * * * *